United States Patent
Makovec et al.

(12) 
(10) Patent No.: US 6,605,722 B2
(45) Date of Patent: Aug. 12, 2003

(54) TYROSINE DERIVATIVES WITH ANTI-LEUKOTRIENEN ACTIVITY

(75) Inventors: Francesco Makovec, Monza (IT); Walter Peris, Milan (IT); Lucio Claudio Rovati, Monza (IT)

(73) Assignee: Rotta Research Laboratorium S.p.A., Milan (IT)

( * ) Notice: Subject to any disclaimer, the term of this patent is extended or adjusted under 35 U.S.C. 154(b) by 0 days.

(21) Appl. No.: 10/203,424

(22) PCT Filed: Feb. 7, 2001

(86) PCT No.: PCT/EP01/01315
§ 371 (c)(1),
(2), (4) Date: Aug. 8, 2002

(87) PCT Pub. No.: WO01/58892
PCT Pub. Date: Aug. 16, 2001

(65) Prior Publication Data
US 2003/0087910 A1 May 8, 2003

(30) Foreign Application Priority Data
Feb. 9, 2000 (IT) .......................... TO20A0127

(51) Int. Cl.$^7$ ................... C07D 215/38; C07D 215/12; A61K 31/47
(52) U.S. Cl. ................ 546/175; 546/171; 546/174; 514/34
(58) Field of Search ................. 546/175, 174, 546/171; 514/311

(56) References Cited

U.S. PATENT DOCUMENTS

| | | | |
|---|---|---|---|
| 4,780,469 A | 10/1988 | Toda et al. | |
| 4,859,692 A | 8/1989 | Bernstein et al. | |
| 5,508,408 A | 4/1996 | von Sprecher et al. | |

FOREIGN PATENT DOCUMENTS

| | | | |
|---|---|---|---|
| DE | 19823722 | * | 12/1999 |
| DE | 198 23 722 A | | 12/1999 |
| EP | 0 335 315 B1 | | 6/1994 |
| EP | 0 480 717 B1 | | 4/1998 |
| WO | WO 96 04246 A | | 2/1996 |
| WO | WO 9604246 | * | 2/1996 |
| WO | WO 96/33181 | | 10/1996 |

OTHER PUBLICATIONS

Brooks, J Jed Chem, vol. 39, No. 14, pp 2629–2654, Jul. 1996.*
Journal of Medicanal Chemistry, vol. 39, No. 14, Jul. 5, 1996, pp. 2629–2654.
"SmithKline Beecham Pharmaceuticals" cysteinyl leukotriene receptor antagonists: Pranlukast (SB 205312; Ono-1078; Onon), Pobilukast (SK&F 104353) and SK & F 106203), Novel Inhibotors of Leukotrienes, Douglas W. P. Hay, 1999, pp. 317–341.

C. D. W. Brooks et al.: "Modulators of Leukotriene Biosynthesis and Receptor Activation" Journal of Medicinal Chemistry, US, American Chemical Society. Washington, vol. 39, No. 14, Jul. 5, 1996, pp. 2629–2654, XP002045087, ISSN: 0022-2623.

* cited by examiner

Primary Examiner—D. Margaret Seaman
(74) Attorney, Agent, or Firm—Sughrue Mion, PLLC

(57) ABSTRACT

Compounds which can be represented by general formula (I) indicated below and in which:

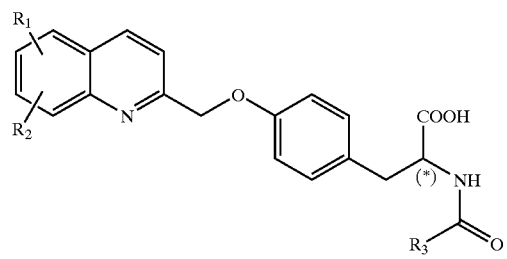

(Formula 1)

$R_1$ and $R_2$ are selected, independently, from hydrogen, an alkyl group having from 1 to 4 carbon atoms, a halogen group such as a fluoro, chloro or bromo group, the methoxy group, the cyano group, or the trifluoromethyl group, and $R_3$ is selected, independently, from a phenyl or a 2 (or 3 or 4)-pyridyl group, unsubstituted or mono- or di-substituted with an alkyl or alkoxy group having from 1 to 4 carbon atoms, with a halogen group such as a fluoro or chloro group, with the trifluoromethyl group, with the cyano group, with the nitro group, with the amino group, or with the phenyl group, a 1 (or 2)-naphthyl group, a 2 (or 3)-indolyl group as such or N-alkylated with an alkyl group having from 1 to 3 carbon atoms, a 2 (or 3, 4, 5, 6, 7 or 8)-quinolinyl or a 1 (or 3, 4, 5, 6, 7 or 8)-isoquinolinyl group, unsubstituted or mono- or di-substituted with a group selected, independently, from the methyl, ethyl, propyl, isopropyl, methoxy, fluoro, chloro, trifluoromethyl, cyano, amino, or nitro groups, a 2 (or 5 or 6)-quinoxalyl group, a (or 4, 5, 6, 7 or 8) cinnolyl group, or a 2 (or 4, 5, 6 or 7)-benzimidazolyl group, and in which the configuration of the chiral centre marked with an asterisk (*) in the general formula (I) may be, independently, L, D or DL (racemic).

9 Claims, No Drawings

TYROSINE DERIVATIVES WITH ANTI-LEUKOTRIENEN ACTIVITY

This is a National stage entry under 35 U.S.C. §371 of Application No. PCT/EP01/01315 filed Feb. 7, 2001; the disclosure of which is incorporated herein by reference.

The subject of the present invention is novel tyrosine derivatives which can be represented by the general formula (I) which is indicated below and in which:

(Formula 1)

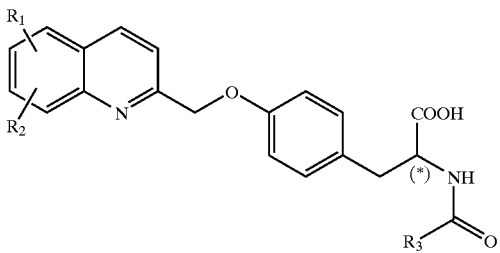

$R_1$ and $R_2$ are selected, independently, from hydrogen, an alkyl group having from 1 to 4 carbon atoms, a halogen group such as a fluoro, chloro or bromo group, the methoxy group, the cyano group or the trifluoromethyl group, and $R_3$ is selected, independently, from a phenyl or a 2 (or 3 or 4)-pyridyl group, unsubstituted or mono- or di-substituted with an alkyl or alkoxy group having from 1 to 4 carbon atoms, with a halogen group such as a fluoro or chloro group, with the trifluoromethyl group, with the cyano group, with the nitro group, with the amino group, or with the phenyl group, a 1 (or 2)-naphthyl group, a 2 (or 3)-indolyl group as such or N-alkylated with an alkyl group having from 1 to 3 carbon atoms, a 2 (or 3, 4, 5, 6, 7 or 8)-quinolinyl or a 1 (or 3, 4, 5, 6, 7 or 8)-isoquinolinyl group, unsubstituted or mono- or di-substituted with a group selected, independently, from the methyl, ethyl, propyl, isopropyl, methoxy, fluoro, chloro, trifluoromethyl, cyano, amino, or nitro groups, a 2 (or 5 or 6)-quinoxalyl group, a 3 (or 4, 5, 6, 7 or 8) cinnolyl group, or a 2 (or 4, 5, 6 or 7)-benzimidazolyl group.

The configuration of the chiral centre marked with an asterisk (*) in the general formula (I) may be, independently, L, D or DL (racemic).

SUMMARY OF THE INVENTION

Preferably, $R_1$ is hydrogen group, $R_2$ is hydrogen or the 7-methyl or 7-fluoro group, and $R_3$ is the 2-quinolinyl group or the 3-isoquinolinyl group.

The compounds of the present invention have been found to be potent receptor antagonists of the cysteinyl-leukotrienes (or $LTD_4$ peptidyl-leukotrienes, hereinafter referred to as leukotrienes).

The leukotrienes are synthesized "de novo" from arachidonic acid associated with cell membranes. They are produced by a wide variety of inflammatory cells such as mast cells, basophils, eosinophils and macrophages. These compounds are considered to be amongst the principal chemical mediators inducing bronchial asthma in man; this seems fully justified by the fact that the pulmonary parenchyma, epithelium and bronchial smooth musculature in man are particularly rich in leukotriene receptors. The receptor stimulation induced by the peptide leukotrienes brings about an immediate contraction of the smooth musculature and increases mucous secretion by the epithelial cells. The compounds of the present invention may therefore be considered usable to advantage in the treatment of various diseases in man which are induced by leukotriene hyper-stimulation such as, for example, bronchial asthma, obstructive lung diseases, hay fever and rhinitis, in the respiratory tract, as well as in allergic conjunctivitis or in other pathological conditions of other organs or regions such as, for example, ulcerative colitis, Crohn's disease, or food allergies and intolerances in the gastrointestinal system, or in the treatment of inflammatory or atherosclerosis-based pathological conditions of the cardiovascular system which are sensitive to leukotriene inhibition.

In addition to the leukotriene receptor antagonists which have recently started to be used for the treatment of asthma, such as montelukast (EP 480717 B1), pranlukast (U.S. Pat. No. 4,780,469) and zafirlukast (U.S. Pat. No. 4,859,692), many publications and patents describe novel compounds with anti-leukotriene activity. Thus, for example, U.S. Pat. No. 5,508,408 describes quinoline derivatives having leukotriene-antagonistic activity, amongst which is the compound iralukast (CGP 45715A), European patent 335 315 B1 describes alkanophenone derivatives, and patent WO 96/33181 describes ethinylthiazole derivatives. A monographic work published in J. Med. Chem. (1996), 39 (2629–2654), also describes the chemical structures and the pharmacological activities of numerous cysteinyl-leukotriene receptor antagonists amongst which, in addition to those already mentioned, are also others such as, for example, the compounds tomelukast, sulukast, ritolukast, verlukast and ablukast. Recently, a monographic work has been published on two antagonists which are structurally correlated with the receptor agonists, that is, pobilukast and SKF 106203, (Novel inhibitors of leukotrienes, G. Folco, B. Samuelsson, R. C. Murphy, Eds., Birkhäuser Verlag, 1999, p. 317). All of this research demonstrates that there is a great therapeutic need to find novel, ever more potent, selective and better tolerated drugs with leukotriene-antagonistic activity. In accordance with this need, the object of the present invention is to make available for therapy novel drugs having a potent and selective leukotriene-antagonist activity for the treatment of all pathological conditions in which a high degree of synthesis and liberation of peptide leukotrienes may assume a primary role, as in the case of allergic diseases in general and of bronchial asthma in particular.

Pharmaceutical forms of the compounds of the invention can be prepared by conventional techniques, for example, as tablets, capsules, suspensions, solutions, aerosols, or patches and can be administered by oral, parenteral, inhalational, transdermal or transmucosal routes, or in other forms suitable for achieving the therapeutic effect such as, for example, delayed-action solid preparations for oral use which permit controlled release of the active substance over time.

The active ingredient is normally administered to the patient with a reference dose variable from 0.01 to 1 mg/kg of body weight per dose. For parenteral administration; the use of a water-soluble salt of the compounds of the invention, such as the sodium salt, or another non-toxic and pharmaceutically acceptable salt is preferable. For the inhalational route, the administration of a water-soluble salt such as, for example, the sodium salt, is also preferable; moreover for this route it is preferable to dispense the active ingredient in the form of a fine, micronized powder having a mean particle diameter preferably of between 1 and 3 microns.

As inactive ingredients, substances commonly used in pharmaceuticals, such as excipients, binders, flavourings, disaggregrants, substances for stimulating transdermal and transmucosal absorption, colourings, humectants, etc., may be used and, for dispensing by means of a pressurized aerosol for inhalation, ecologically acceptable propellants or mixtures of propellants are also used.

The method for the preparation of the derivatives of the invention consists of a series of reactions which comprise:

a) reacting methyl tyrosine ester in the desired configuration with the aromatic or heterocyclic acid of formula (V):

in which $R_3$ has the meaning given above, by the mixed anhydride method, in an inert anhydrous solvent and at a temperature of between −5° C. and +15° C., to give the N-acyl tyrosine derivatives of formula (IV) (see the general synthesis scheme, step 1);

b) reacting the compounds of formula (IV) with the halogenomethyl quinoline of formula (III):

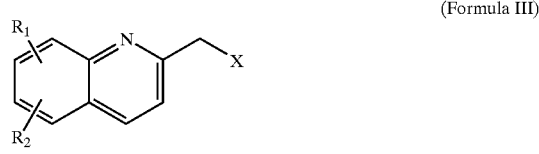

in which $R_1$ and $R_2$ have the meanings given above and X may be chloro or bromo, in the presence of a base such as, for example, potassium carbonate, in an inert solvent such as, for example N,N-dimethyl formamide (DMF), and at a temperature of between 20° C. and the reflux temperature of the solvent used, to give the esters of formula (II), in which $R_1$, $R_2$ and $R_3$ have the meanings given above (see the general synthesis scheme, step 2);

c) hydrolyzing the esters of formula (II):

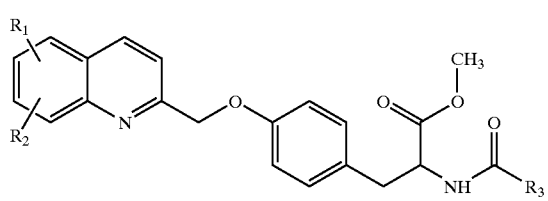

dissolved in an inert solvent such as, for example, methanol, with an inorganic base such as, for example, sodium hydroxide, in a molar ratio of from 1 to 1.5, to give the corresponding final derivatives of formula (I) in which $R_1$, $R_2$ and $R_3$ have the meanings given above, according to the general synthesis scheme, step 3.

The aromatic or heterocyclic acids of formula (V), as well as the halogenomethyl quinoline of formula (III), are commercially available or are prepared by conventional methods in accordance with existing literature.

The final derivatives of formula (I) are obtained in the L, D or DL (racemic) forms, according to whether the starting compound was L, D or DL tyrosine.

General Synthesis Scheme (Scheme 1)

Step 1

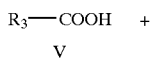

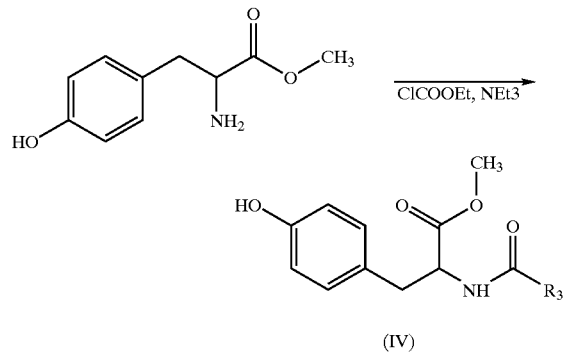

Step 2

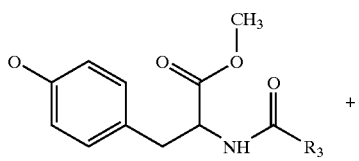

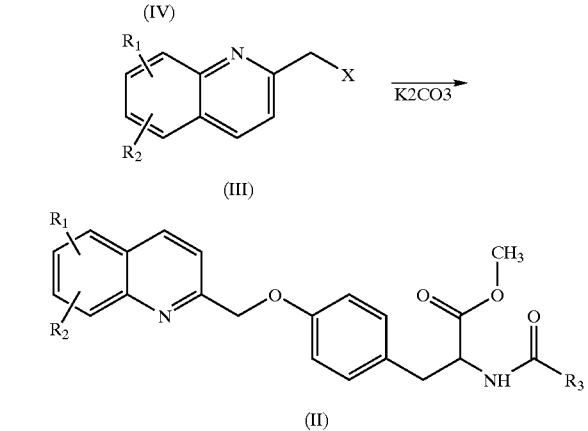

Step 3

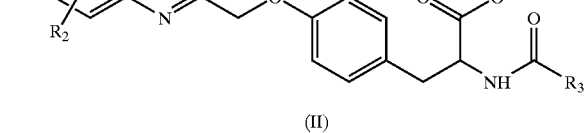

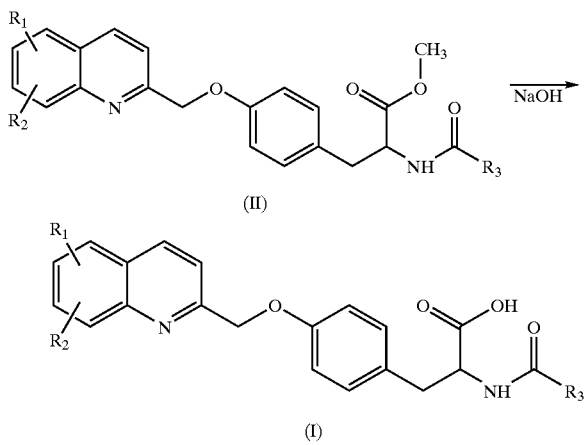

The following examples are given below to illustrate the invention further.

EXAMPLE 1

Preparation of N-quinaldoyl-D,L-tyrosine methyl ester 20 g of quinaldic acid (0.115 moles) was dissolved in 200 ml of tetrahydrofuran. The solution was cooled to −10° C. and 16.4 ml of triethylamine (0.1178 moles) was added with stirring. A solution of 11.3 ml of ethyl chloroformate (0.1178 moles) was added dropwise, still with stirring. Upon completion, stirring was continued at −10° C. for about a further 15 minutes and then a solution of 25.0 g of D,L-tyrosine methyl ester (0.127 moles) in 50 ml of tetrahydrofuran was added dropwise, the temperature was then allowed to rise to ambient temperature, and stirring was continued overnight. The suspension was concentrated under vacuum, the residue was taken up with 1M citric acid and ethyl ether, filtered, washed with water and ethyl ether, and dried, to give 32.5 g.

Formula: $C_{20}H_{18}N_2O_4$ (M.W. 350.4). Yield 80%. TLC (Toluene/ethyl acetate 7/3) rf 0.28; (ethyl acetate/MetOH 9/1) rf 0.85, M.P. : 218° C.

All of the compounds of formula (IV) were synthesized with the use of the same method (see Scheme 1, Step 1).

EXAMPLE 2

Preparation of O-(2-quinolinylmethyl)-N-quinaldoyl-D,L-tyrosine methyl ester 16 g of N-quinaldoyl-D,L-tyrosine methyl ester (0.046 moles), 11 g of 2-chloromethyl quinoline hydrochloride (0.05 moles) and 19 g of potassium carbonate (0.137 moles) were suspended in 200 ml of DMF. The suspension was heated to 80° C. for 8 hours with stirring. The suspension was cooled to ambient temperature, poured into ice and acidified with citric acid. Extraction was performed with ethyl acetate and the organic phase was washed with water and extracted again with 2N hydrochloric acid. The acid aqueous phase was washed with ether, alkalified with $NaHCO_3$ and extracted again with ethyl acetate. The organic phase was washed with water, acidified and evaporated under vacuum. 20 g of a dense oil was obtained and was used in the next step, as it was, without further purification.

Formula: $C_{30}H_{25}N_3O_4$ (M.W. 491.5), Yield 90%. TLC: (ethyl acetate/MetOH 9/1) rf 0.84.

All of the intermediate compounds of formula (II) were synthesized with the use of the same method (see Scheme 1, Step 2).

EXAMPLE 3

Preparation of O-(2-quinolinylmethyl)-N-quinaldoyl-D,L-tyrosine. (Compound 1 of Table 1)

13 g of O-(2-quinolinylmethyl)-N-quinaldoyl-D,L-tyrosine methyl ester (0.026 moles) was dissolved in 260 ml of methanol to which 15 ml of 2N sodium hydroxide (0.030 moles) was added with stirring. After 4 hours, the solution was concentrated under vacuum, the residue, taken up with water, was acidified to acid pH with citric acid, filtered, washed with water, and ethyl ether, and recrystallized from a 1/1 (v/v) acetonitrile/isopropanol mixture. 9.9 g was obtained.

Formula: $C_{29}H_{23}N_3O_4$ (M.W. 477.5). Yield 80%. TLC: (isoamyl alcohol/acetone/water 5/2/1) rf 0.49; (ethyl acetate/MetOH 9/1) rf 0.08. M.P. 235° C. HPLC: retention time (rt) 10.0±0.5 minutes. HPLC conditions: Symmetry C8 column, 4.6×150 mm, eluent 0.01M $KH_2PO_4$/MetOH 35/65 (pH 4.1), flow 1 ml/min, 233 nm UV detector.

NMR (DMSO-d6), ppm: 3,20 (bd, 2H); 4.77 (m, 1H); 5.29 (s, 2H); 6.94 (d, 2H); 7.21 (d, 2H); 7.39–8.62 (m, 12 H); 8.79 (d, 1H); 11.0 (bs, 1H).

EXAMPLE 4

Preparation of O-(7-fluoro-2-quinolinylmethyl)-N-quinaldoyl-D,L-tyrosine. (Compound 17 of Table 1)

The method followed for the preparation of the compound was similar to that described in Examples 1–3 and in accordance with Scheme 1. 7-fluoro-2-chloromethyl quinoline was used instead of 2-chloromethyl quinoline (Example 2). The overall yield was 55%.

Formula: $C_{29}H_{22}FN_3O_4$ (M.W. 495.5). M.P.: 248° C. HPLC: rt 10.8±0.2 minutes. Chromatography conditions were identical to those given in Example 3.

NMR (DMSO-d6), ppm: 3.19 (bd, 2H); 4.76 (m, 1H); 5.28 (s, 2H); 6.92 (d, 2H); 7.20 (d, 2H); 7.33–8.62 (m, 11H); 8.78 (d, 1H); 11.0 (bs, 1H).

EXAMPLE 5

Preparation of O-(7-fluoro-2-quinolinylmethyl)-N-quinaldoyl-L-tyrosine. (Compound 18 of Table 1)

The method followed for the preparation of the compound was similar to that described for Example 4, with the use of L-tyrosine instead of D,L tyrosine.

The overall yield was 49%.

Formula: $C_{29}H_{22}FN_3O_4$ (M.W. 495.5). M.P. 229° C. Rotatory power $[\alpha]^{21}D=-40°$ (DMF). Optical purity (HPLC after derivatization): >90%.

Analytical conditions for the derivatization: a solution of the product under test was prepared at a concentration of 0.5 mg/ml in a solution of triethylamine in MeCN (7 μL in 10 ml); 0.4 ml of this solution was cooled to −5/−10° C. After about 5 minutes 0.2 ml of a solution of ethyl chloroformate in MeCN (56 μl in 10 ml of MeCN) was added and the mixture was left to react cold for 10 minutes. 0.2 ml of a solution of 1-phenylalaninamide in MeCN (170 mg in 5 ml of MeCN) was added and the mixture was left to react cold for 20 minutes. The mixture was diluted with 5 ml of water and the volume was brought to 10 ml with MeOH. After derivatization, the compound was injected into a column (50 μl) in the conditions described for the achiral HPLC (see Example 3).

Retention time: 22.6±0.7 minutes.

EXAMPLE 6

Preparation of O-(7-fluoro-2-quinolinylmethyl)-N-quinaldoyl-D-tyrosine. (Compound 19 of Table 1)

The method followed for the preparation of the compound was similar to that described for Example 4, with the use of D-tyrosine instead of D,L tyrosine.

The overall yield was 45%.

Formula: $C_{29}H_{22}FN_3O_4$ (M.W. 495.5) M.P.: 227° C. Rotatory power $[\alpha]^{21}D=+44°$ (DMF). Optical purity (HPLC after derivatization): ≧90%.

The derivatization method and the chromatography conditions were identical to those described for Compound 18 (Example 5).

Retention time: 23.8±0.7 minutes.

Some derivatives of formula (I)

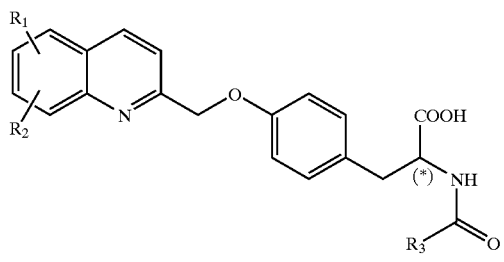

(Formula 1)

produced in accordance with the invention, with some chemical and physical characteristics which identify them, are given in Table 1 below, without thereby in any way limiting the spirit or the scope of the invention.

time was 30 minutes at 25° C. The separation of the bound from the free was performed by rapid filtration on Whatman GF/B paper filters. The results obtained are shown in Table 2 in which the $IC_{50}$, that is, the concentration (nanomolar) of antagonist capable of displacing 50% of the $[^3H]$-$LTD_4$ ligand from the receptor, is given for some of the compounds of the invention already mentioned by way of example in Table 1.

TABLE 2

Inhibition of the binding of $[^3H]$-$LTD_4$ to guinea-pig lung membranes

| Compound | $IC_{50} \times 10^{-9}$ M |
|---|---|
| 1 | 20.0 |
| 2 | 190 |
| 3 | 98.1 |
| 4 | 110 |

TABLE I

| Compound[a] | $R_2$ | $R_3$ | Rough Formula | M.P. (crystallization solvent[b]) | TLC $(R_f)$[c] |
|---|---|---|---|---|---|
| 1 | H | 2-quinolinyl | $C_{29}H_{23}N_3O_4$ | 235° C. (B) | 0.35 |
| 2 | H | phenyl | $C_{26}H_{22}N_2O_4$[d] | 140° C. (A) | 0.27 |
| 3 | H | 4-chlorophenyl | $C_{26}H_{21}ClN_2O_4$ | 197° C. (A) | 0.34 |
| 4 | H | 3-chlorophenyl | $C_{26}H_{21}ClN_2O_4$ | 187° C. (A) | 0.35 |
| 5 | H | 4-methoxyphenyl | $C_{27}H_{24}N_2O_5$ | 212° C. (A) | 0.36 |
| 6 | H | 4-trifluoromethylphenyl | $C_{27}H_{21}F_3N_2O_4$ | 211° C. (A) | 0.37 |
| 7 | H | 2-biphenyl | $C_{32}H_{26}N_2O_4$ | 155° C. (A) | 0.43 |
| 8 | H | 4-biphenyl | $C_{32}H_{26}N_2O_4$[d] | 230° C. (D) | 0.40 |
| 9 | 7-Cl | 4-biphenyl | $C_{32}H_{25}ClN_2O_4$ | 193° C. (A) | 0.65 |
| 10 | H | 2-pyridyl | $C_{25}H_{21}N_3O_4$ | 171° C. (A) | 0.16 |
| 11 | H | 2-naphthyl | $C_{30}H_{24}N_2O_4$ | 196° C. (A) | 0.39 |
| 12 | H | 3-quinolinyl | $C_{29}H_{23}N_3O_4$ | 230° C. (A) | 0.25 |
| 13 | H | 6-quinolinyl | $C_{29}H_{23}N_3O_4$ | 248° C. (A) | 0.16 |
| 14 | H | 8-quinolinyl | $C_{29}H_{23}N_3O_4$ | 141° C. (D) | 0.32 |
| 15 | 7-Me | 2-quinolinyl | $C_{30}H_{25}N_3O_4$ | 214° C. (A) | 0.43 |
| 16 | H | 4-quinolinyl | $C_{29}H_{23}N_3O_4$ | 224° C. (A) | 0.10 |
| 17 | 7-F | 2-quinolinyl | $C_{29}H_{22}FN_3O_4$ | 248° C. (B) | 0.47 |
| 18 (L) | 7-F | 2-quinolinyl | $C_{29}H_{22}FN_3O_4$ | 229° C. (B) | 0.47 |
| 19 (D) | 7-F | 2-quinolinyl | $C_{29}H_{22}FN_3O_4$ | 227° C. (B) | 0.47 |
| 20 | H | 1-isoquinolinyl | $C_{29}H_{23}N_3O_4$ | 157° C. (A) | 0.25 |
| 21 | H | 3-isoquinolinyl | $C_{29}H_{23}N_3O_4$ | 204° C. (A) | 0.32 |
| 22 | 7-F | 3-isoquinolinyl | $C_{29}H_{22}FN_3O_4$ | 227° C. (E) | 0.51 |
| 23 | H | 2-indolyl | $C_{28}H_{23}N_3O_4$ | 223° C. (A) | 0.42 |
| 24 | H | 3-indolyl | $C_{28}H_{23}N_3O_4$ | 226° C. (A) | 0.41 |
| 25 | H | 2-indolyl-N-methyl | $C_{29}H_{25}N_3O_4$ | 198° C. (B) | 0.28 |
| 26 | H | 3-indolyl-N-methyl | $C_{29}H_{25}N_3O_4$ | 180° C. (A) | 0.20 |
| 27 | H | 2-quinoxalinyl | $C_{28}H_{22}N_4O_4$ | >240° C. (A) | 0.17 |
| 28 | H | 4-cinnolinyl | $C_{28}H_{22}N_4O_4$ | 232° C. (A) | 0.14 |
| 29 | H | 6-benzimidazolyl | $C_{27}H_{22}N_4O_4$ | >250° C. (A) | 0.29 |
| 30 | H | 2-(5-phenylpyridyl) | $C_{31}H_{25}N_3O_4$ | 170° C. (F) | 0.44 |

For all of the compounds $R_1$ = H;
[a]All of the compounds except those indicated are in the (D, L) configuration.
[b]Crystallization solvent: A (MeCN); B (MeCN/i-PrOH 1:1); C (AcOEt/Et$_2$O 1:1); D (MeCN/i-PrOH 3:1); E (MeCN/i-PrOH 2:1); F (MeCN/i-PrOH/H$_2$O 1:1.3).
[c]Eluent: isoamyl alcohol/acetone/water (5/2/1) (v/v).
[d]Isolated as hydrochloride Description of Pharmacological Activity a) The antagonistic activity of the compounds of the invention at the level of the peptide-leukotriene receptor was assessed as their capacity to inhibit the binding of the specific agonist $[^3H]$-$LTD_4$ to guinea-pig lung membranes. The method described by Frey et al. [Eur. J. Pharmacol. 244 (1993): 239–250] was followed, with slight modifications.

The concentration of radio-ligand $[^3H]$-$LTD_4$ used was 0.3 nM with a membrane content corresponding to a protein content of 100–120 μg of protein per sample; the incubation TABLE 2-continued Inhibition of the binding of $[^3H]$-$LTD_4$ to guinea-pig lung membranes

| Compound | $IC_{50} \times 10^{-9}$ M |
|---|---|
| 5 | 117 |
| 6 | 42.7 |
| 7 | 181 |

TABLE 2-continued

Inhibition of the binding of [$^3$H]-LTD$_4$ to guinea-pig lung membranes

| Compound | IC$_{50}$ × 10$^{-9}$ M |
|---|---|
| 8 | 61.7 |
| 9 | 217 |
| 10 | 32.3 |
| 11 | 39.0 |
| 12 | 76.0 |
| 13 | 135 |
| 14 | 64.0 |
| 15 | 11.3 |
| LTD$_4$ | 3.2 |
| 16 | 200 |
| 17 | 7.9 |
| 18 | 5.5 |
| 19 | 12.2 |
| 20 | 64.1 |
| 21 | 9.7 |
| 22 | 5.3 |
| 23 | 103 |

TABLE 2-continued

Inhibition of the binding of [$^3$H]-LTD$_4$ to guinea-pig lung membranes

| Compound | IC$_{50}$ × 10$^{-9}$ M |
|---|---|
| 24 | 55.3 |
| 25 | 34.8 |
| 26 | 50.8 |
| 27 | 161 |
| 28 | >300 |
| 29 | 90.3 |
| 30 | 24.1 |

It can be seen from the data given in Table 2 that some of the compounds of the invention are potent inhibitors of the binding of [$^3$H]=LTD$_4$ to the receptors of guinea-pig lung membranes. Thus, for example, Compounds 17, 18 and 22, in experimental model, have an affinity which is comparable, at nanomolar level, to that of the specific LTD$_4$ agonist.

b) For some of the compounds which were most active in inhibiting the binding of [$^3$H]-LTD$_4$ to guinea-pig lung membranes, it was desired to assess the anti-leukotriene activity against LTD$_4$ in a functional test using isolated guinea-pig trachea according to the method of Jones et al. [Can. J. Physiol. Pharmacol. 67 (1989): 17–28], with slight modifications. Cumulative LTD$_4$ dose-response curves were effected in the absence (control preparation) and in the presence of antagonist added to the bath, for organs isolated 15 minutes before the cumulative LTD$_4$ curve was effected. The results were expressed as the effect as a percentage of the maximum contraction induced by 300 μM acetylcholine. The results thus obtained are given in Table 3.

The compounds of the invention which were examined produced a concentration-dependent shift to the right of the cumulative dose-response curves of contraction induced by LTD$_4$ in the guinea-pig trachea strips. From an analysis according to Schild of the curves thus obtained, it was possible to calculate the relative pA$_2$; the compounds of the invention which were examined were also found to be potent leukotriene antagonists in this functional test: for example, Compound 22 had a calculated pA$_2$ of 8.76, equivalent to a K$_b$ value of 1.73 nM.

TABLE 3

Antagonism exerted by the compounds of the invention on contractions induced by LTD4 (cumulative dose-response curves) on isolated guinea-pig trachea in vitro, and regression lines and pA$_2$ calculated according to Schild(*)

| | Concentrations used (nM) and ED50 (nM) | | | | | | |
|---|---|---|---|---|---|---|---|
| Compound | Solvent | 3 | 10 | 30 | 100 | 300 | Equations of the straight lines |
| 1 | 2.89 | — | 4.53 | 15.31 | 31.75 | — | log (A'/A − 1) = 9.78 − 1.24B<br>pA$_2$ = 7.88 |
| 17 | 2.37 | 4.69 | — | 9.48 | — | 19.78 | log (A'/A − 1) = 3.75 − 0.44B<br>pA$_2$ = 8.53 |
| 22 | 2.09 | — | 8.03 | 13.71 | 25.39 | — | log (A'/A − 1) = 5.2 − 0.59B<br>pA$_2$ = 8.76 |

Where: A'/A = ratio between the concentration of the agonist, with and without antagonist, which causes 50% of the maximum contraction
B = negative logarithm of the concentration of antagonist
(*) Van Rossum et al. (Arch. Int. Pharmacodyn. Ther. 143 (1963) p. 240)

Activity in vivo

In addition to the potency shown in vitro in the models given by way of example above, an advantageous and important characteristic of the compounds of the present invention is their optimal oral bio-availability. Thus, for example, Compound 1, administered to rats at a dose of 20 mg/kg, provided a maximum plasma concentration (C$_{MAX}$) of about 20 mcg/ml 1 hour after administration. The AUC calculated was about 50 mcg/ml.h and, even 8 h after administration, the plasma levels gave a concentration of more than 2 mcg/ml.

Both of these characteristics, that is, optimal bio-availability and the potency exhibited in the in vitro tests explain the high activity of some of the compounds of the invention in vivo. Thus, for example, Compound 17 at a dose of 0.3 mg/kg administered orally 30 minutes before the challenge performed with aerosolized ovalbumin (0.5% w/v in saline) in guinea-pigs previously sensitized according to the method described by Makovec et al. [J. Med. Chem. 35 (1992), 3633–3640] completely inhibited the signs of bronchoconstriction, which were recorded as the first appearance of abdominal contractions.

The compounds according to the invention also have a low toxicity profile. Thus, for example, Compound 17 which, as stated, is capable of performing its oral activity at a dose of 0.3 mg/kg, has an acute toxicity (LD$_{50}$) in mice which is greater than 50 mg/kg intravenously and greater than 300 mg/kg orally. The fact that the acute toxic dose in mice by the oral route is more than 1000 times greater than the pharmacologically effective dose permits the prediction that Compound 17, as well as other subjects of the invention, can exhibit an extremely favourable therapeutic profile.

What is claimed is:

1. Compounds which can be represented by general formula (I) indicated below and in which:

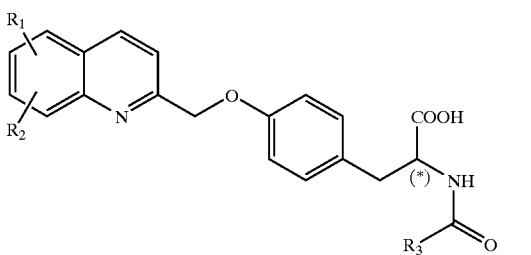

(Formula 1)

$R_1$ and $R_2$ are selected, independently, from hydrogen, an alkyl group having from 1 to 4 carbon atoms, a halogen group such as a fluoro, chloro or bromo group, the methoxy group, the cyano group, or the trifluoromethyl group, and $R_3$ is selected, independently, from a phenyl or a 2 (or 3 or 4)-pyridyl group, unsubstituted or mono- or di-substituted with an alkyl or alkoxy group having from 1 to 4 carbon atoms, with a halogen group such as a fluoro or chloro group, with the trifluoromethyl group, with the cyano group, with the nitro group, with the amino group, or with the phenyl group, a 1 (or 2)-naphthyl group, a 2 (or 3)-indolyl group as such or N-alkylated with an alkyl group having from 1 to 3 carbon atoms, a 2 (or 3, 4, 5, 6, 7 or 8)-quinolinyl or a 1 (or 3, 4, 5, 6, 7 or 8)-isoquinolinyl group, unsubstituted or mono or di-substituted with a group selected, independently, from the methyl, ethyl, propyl, isopropyl, methoxy, fluoro, chloro, trifluoromethyl, cyano, amino, or nitro groups, a 2 (or 5 or 6)-quinoxalyl group, a 3 (or 4, 5, 6, 7 or 8) cinnolyl group, or a 2 (or 4, 5, 6 or 7)-benzimidazolyl group, and in which the configuration of the chiral centre marked with an asterisk (*) in the general formula (I) may be, independently, L, D or DL (racemic).

2. Compounds according to claim 1, of general formula (I), in which $R_1$ is hydrogen (H), $R_2$ is H or the 7-methyl or the 7-fluoro group, and $R_3$ is the 2-quinolinyl group or the 3-isoquinolinyl group, and the stereochemistry of the chiral centre marked with an asterisk (*) in (I) is L, D or DL (racemic).

3. A pharmaceutical preparation comprising, as an active substance, at least one of the compounds according to claim 1 or a pharmaceutically acceptable salt thereof.

4. A pharmaceutical preparation according to claim 3 for use in the therapeutic treatment of pathological conditions sensitive to leukotriene inhibition.

5. A pharmaceutical preparation according to claim 3 for use in the therapeutic treatment of pathological conditions of the respiratory system connected with allergic or inflammatory phenomena such as, for example, bronchial asthma, obstructive lung diseases, hay fever, allergic rhinitis, or in the treatment of irritative eye conditions such as, for example, allergic conjunctivitis.

6. A pharmaceutical preparation according to claim 3 for use in the therapeutic treatment of pathological conditions of the gastrointestinal tract such as, for example, ulcerative colitis, Crohn's disease, and food allergies and intolerances.

7. A pharmaceutical preparation according to claim 3 for use in the therapeutic treatment of inflammatory or atherosclerosis-based pathological conditions of the cardiovascular system, which are sensitive to leukotriene inhibition.

8. A pharmaceutical preparation according to claim 3, further comprising pharmaceutically acceptable inactive ingredients selected from the group which consists of vehicles, binders, flavourings, sweeteners, disaggregants, preservatives, humectants and mixtures thereof, or ingredients which facilitate transdermal or transmucosal absorption, or which permit the controlled release of the active substance over time or, for dispensing by means of pressurized aerosol for inhalation, ecologically acceptable propellants or mixtures of propellants.

9. A method for the preparation of a derivative of general formula (I) in which $R_1$, $R_2$ and $R_3$ have the meanings given in claim 1 and in which the substituents at the chiral centre marked with an asterisk (*) have the L, D, or DL (racemic) configuration, which comprises the steps of:

a) reacting methyl tyrosine ester in the desired configuration with an aromatic or heterocyclic acid of formula (V):

$R_3$—COOH (V)

in which $R_3$ has the meaning given above, by the mixed anhydride method, in an inert anhydrous solvent and at a temperature of between –5° C. and +15° C., to give the N-acyl tyrosine derivatives of formula (IV):

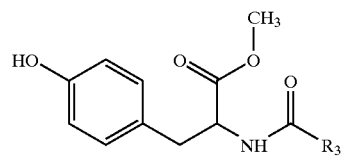

b) reacting the compounds of formula (IV) with the halogenomethyl quinoline of formula (III):

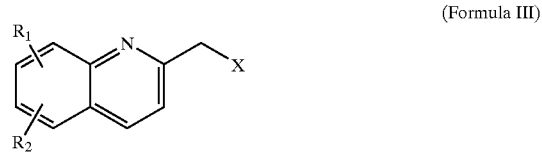

(Formula III)

in which $R_1$ and $R_2$ have the meanings given above and X may be chloro or bromo, in the presence of a base such as, for example, potassium carbonate, in an inert solvent such as, for example N,N-dimethyl formamide (DMF), and at a temperature of between 20° C. and the reflux temperature of the solvent used, to give the esters of formula (II), in which $R_1$, $R_2$ and $R_3$ have the meanings given above:

c) hydrolyzing the esters of formula (II):

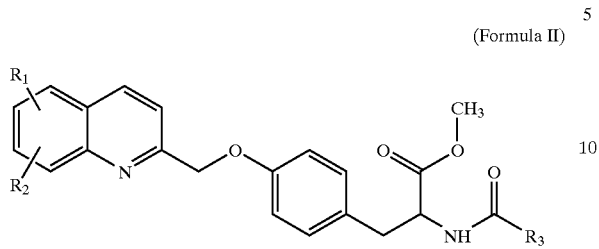
(Formula II)

dissolved in an inert solvent such as, for example, methanol, with an inorganic base such as, for example, sodium hydroxide, in a molar ratio of from 1 to 1.5, to give the corresponding final derivatives of formula (I):

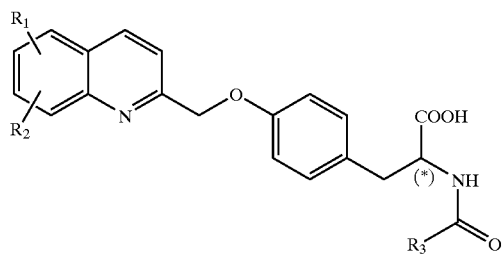
(Formula 1)

in which $R_1$, $R_2$ and $R_3$ have the meanings given above, the final compounds of formula (I) being recovered from the reaction mass as such or as pharmaceutically acceptable salts, and being purified by conventional methods.

* * * * *

UNITED STATES PATENT AND TRADEMARK OFFICE
CERTIFICATE OF CORRECTION

PATENT NO. : 6,605,722 B2
DATED : August 12, 2003
INVENTOR(S) : Francesco Makovec, Walter Peris and Lucio Claudio Rovati It is certified that error appears in the above-identified patent and that said Letters Patent is hereby corrected as shown below:

Title page,
Item [54], Title, please change "ANTI-LEUKOTRIENEN" to -- ANTI-LEUKOTRIENE --.

Signed and Sealed this

Twenty-fifth Day of January, 2005

JON W. DUDAS
*Director of the United States Patent and Trademark Office*